United States Patent [19]

Hyldon et al.

[11] 4,175,124

[45] Nov. 20, 1979

[54] METHOD OF TREATING HYPERCHOLESTEROLEMIA

[75] Inventors: Roy G. Hyldon; John S. O'Mahony, both of Crystal Lake, Ill.

[73] Assignee: The Quaker Oats Company, Chicago, Ill.

[21] Appl. No.: 866,100

[22] Filed: Dec. 30, 1977

[51] Int. Cl.$^2$ ................... A61K 31/70; A61K 31/715
[52] U.S. Cl. ...................................... 424/180; 536/114
[58] Field of Search .................. 424/180, 182; 536/114

[56] References Cited

U.S. PATENT DOCUMENTS

| | | | |
|---|---|---|---|
| 3,081,226 | 3/1963 | Di Luzio et al. | 167/55 |
| 3,148,114 | 9/1964 | Fahrenbach | 424/180 |
| 3,415,927 | 12/1968 | Butensky | 424/180 |
| 3,849,554 | 11/1974 | Winitz | 424/180 |
| 4,028,468 | 6/1977 | Hohner et al. | 426/436 |
| 4,039,659 | 8/1977 | Gordon | 424/115 |

*Primary Examiner*—Johnnie R. Brown
*Assistant Examiner*—Blondel Hazel
*Attorney, Agent, or Firm*—Charles J. Hunter

[57] ABSTRACT

A method of treating Hypercholesterolemia in mammals is described herein. The blood cholesterol level in mammals is reduced by orally administering an effective amount of oat or barley gum.

8 Claims, No Drawings

METHOD OF TREATING HYPERCHOLESTEROLEMIA

BACKGROUND OF THE INVENTION

1. FIELD OF THE INVENTION

This invention relates to a method of treating Hypercholesterolemia in mammals. More particularly, it relates to a method of reducing cholesterol levels in mammals by orally administering oat or barley gums.

2. DESCRIPTION OF THE PRIOR ART

Hypercholesterolemia has been related to the incidence of atherosclerosis in several studies. The latter disease is characterized by thickening of the intima, reduction in artery diameter and loss of elasticity of the arteries due to localized accumulation of lipids. These lipids are comprised majorally of cholesterol and triglycerides. The fact that cholesterol, a naturally occurring sterol, is a major component of human atherosclerotic lesions; combined with the well established correlation between the concentration of lipoprotein cholesterol in plasma and the incidence of atherosclerotic heart disease supports the fact that cholesterol may be essential to the development of atherosclerosis.

Restricting the diet in regard to cholesterol and also to fats is looked upon with favor by some investigators for the prevention of atherosclerosis, and is regarded as of less importance by others. It has been well documented that mammals can synthesize cholesterol from simpler compounds, such as acetate. By use of the isotope tracer method, it has been discovered that cholesterol is synthesized by practically every tissue in the body. Thus, it is evident that dietary restrictions alone cannot be expected to be successful in all cases of hypercholesterolemia.

In the past, attempts have been made to lower the level of cholesterol in the blood serum by the oral feeding of various substances. Typical of such substances are pectin, lecithin, and corn oil. Many polysaccharide materials including pectin have been tested in animals as hypocholesterolimic agents. Pectin has been studied rather extensively in both animals and humans with moderate success. Guar, methomucil, alginate, locust bean gum and carageenan have also been tested with reasonable good success. Other lesser known polysaccharides such as Konjac mannan and Bengal gram polysaccharide have been shown to be effective hypocholesterolemic agents in rats and humans respectively. The mechanism of depression of these polysaccharides is reported to be increased degradation of cholesterol to bile acids and increased fecal excretion of bile salts.

The most common therapy for hypercholesterolemia its a dietary regimen with or without concomitant drug therapy. The diet recommended is low in fat and devoid as far as possible of animal fat. This regimen requires reduced consumption, or complete elimination, from the diet of such nutritious foods as eggs, meat and milk products. The drug therapy has used several drug materials to depress serum cholesterol in animal and human studies. The most effective materials, cholestyramine and colestid, are effective because they sequester bile acids which are excreted in the fecal material. These bile acids are derived from increased catabolism of low density lipoproteins. Drug therapy results in a decrease in blood serum cholesterol which can be readily measured.

Many of the most effective drugs used to treat hypercholesterolemia have side effects varying in degree of severity from constipation to increasing the incidence of the disease the drug is attempting to prevent. Thus, there is a need and desire for materials which have little or no side effects and which can have a cholesterol depressive effect equal to or better than the common drugs.

According to the present invention, we have found that a polysaccharide commercially prepared from *Avena sativa* species is effective in depressing serum cholesterol in mammals.

Oat gum is a water soluble carbohydrate present in dehulled oats (*Avena sativa*) at a level of 3–5% on a dry weight basis. It is a high molecular weight polymer of glucose with alternating cycles of beta 1,3 linkages followed by beta 1,4 linkages. The ratio between the number of beta 1,3 linkages to beta 1,4 linkages is 1 to 3.2. Oat gum differs from other polymers of glucose by those specific linkages present between the glucose molecules. In this respect it is similar to a gum obtainable from the Hordeum species. For example, in starch, 1,4 alpha linkages form the linear part of the polymer, with 1,6 alpha linkages present at the branched points on the polymer. In cellulose, the glucose monomer is polymerized via 1,4 beta linkages. The oat gum is not digested in the stomach or small intestine because of the lack of beta glucosidase enzymes but is digested readily in the cecum and large intestine by bacterial enzymes. The gum can be readily extracted from oats and purified.

Purified oat gum has been shown to be effective in rats as a hypocholesterolemic agent at levels of 0.01% to 0.1% of body weight. The mechanism of this depression is by increased catabolism of cholesterol and increased fecal bile salts excretion without changing the cholesterol synthesis.

Because of the ability of oat gum to increase the fecal bile acid excretion while being readily digested in the large intestine leads one to suggest that it would have certain advantages over synthetic polymers which are presently used in the treatment of hypercholesterolemia. This is particularly true in the case of polymers such as cholestyramine which has been reported to increase the fecal excretion of fat soluble vitamins on prolonged usage. Secondly, the oat gum acts as a mild laxative in contrast to cholestyramine, which has been reported to be constipative. Thirdly, it should be more desirable to use natural materials in the treatment of hypercholesterolemia.

Barley, another gum derived from cereals may also be used in the present invention. The cereals comprise a group of plants from the grass family, Gramineae, whose seeds are valuable for food and for making cereal gums. In its broadest sense, the term gum is applied to a wide variety of materials with "gummy" characteristics. These include such hydrophobic substances as rubber, chicle for chewing gum and rosin, as well as a large group of hydrophilic substances that are plant polysaccharides or their derivatives. It is this latter group of oat and barley cereal plant polysaccharides that constitutes the gums used in the present invention.

The method of administering the cereal gums of the present invention is limited to oral administration. The cereal gums of the present invention may be orally administered for example, with an inert diluent or with an assimilable edible carrier, or it may be enclosed in hard or soft gelatin capsules, or it may be compressed into tablets, or it may be incorporated directly with the food of the diet. It is an advantage of the present invention that the oat gum may be orally administered in any convenient manner.

The amount of a single dose or of a daily dose to be given will vary with the size of the animal to be treated, but should be such as to give a proportionate dosage of 0.02 grams to 0.2 grams per pound of body weight per day. In terms of the total weight of oat or barley gum, the dosage is usually from about 1 gram to about 4 grams. As indicated previously, in one embodiment of our invention, it is preferred to incorporate the cereal gum directly in the food of the diet. Any suitable method for dispersing the cereal gum uniformly throughout the food can be used. The amount of cereal gum added to the diet may be varied but it is ordinarily found that an amount within the range of about 0.02 grams to about 0.2 grams per pound of body weight per day promotes the maximum lowering of blood cholesterol.

The following examples illustrate the hypocholesterolemic effect of cereal gum and the method of administering cereal gum whereby a lowering of blood cholesterol is obtained.

EXAMPLE 1

Male and female Wistar rats all six weeks old and weighing between 230 and 300 g were divided into groups of 8 rats of each sex. One group served as a control and the other three groups were used as test groups. All four groups were fed for four weeks the following diet with the test material added at the percentages indicated later. The composition of the diet is shown as percentage by weight.

|  | Percent |
| --- | --- |
| Vitamin free casein | 16.3 |
| Corn oil | 4.0 |
| Hydrogenated coconut oil | 11.0 |
| Corn starch | 59.3 |
| Wood cellulose | 2.0 |
| Salt Mix XIV | 4.0 |
| Vitamin Mix | 2.2 |
| Cholesterol | 1.0 |
| Cholic acid | 0.2 |

The test groups received the following levels of oat gum: 0.01 percent, 0.03 percent and 0.07 percent of body weight of oat gum per day. This level was achieved by measuring feed intake for one week prior to test and then adding the appropriate amount of gum to the individual diets. Blood serum cholesterol determinations were made at 2 and 4 weeks of the test period. The results were as follows in mg/dl.

|  | 2 Weeks | | 4 Weeks | |
| --- | --- | --- | --- | --- |
|  | Male | Female | Male | Female |
| Control | 228 | 331 | 203 | 752 |
| Test Level 1(.01%) | 185 | 326 | 152 | 391 |
| Test Level 2(.03%) | 175 | 281 | 140 | 418 |
| Test Level 3(.07%) | 147 | 301 | 156 | 477 |

EXAMPLE 2

Adult male Wistar rats were fed diets containing cholesterol but no bile salts. The diet was as follows:

| Diet Composition | Percent |
| --- | --- |
| Casein | 11.5 |
| Fat (P/S 1) | 22.0 |
| White Flour | 60.0 |
| Mineral Mix | 4.0 |
| Vitamin Mix | 1.0 |
| Methionine | 0.3 |
| Choline Chloride | 0.2 |
| Cholesterol | 1.0 |

Oat gum was fed at 0.05 percent and 0.1 percent of body weight per day. The serum cholesterol levels were determined after 4 weeks feeding. The results were as follows:

|  | mg/dl |
| --- | --- |
| Control | 145 |
| .05% Oat Gum | 118 |
| .10% Oat Gum | 102 |

EXAMPLE 3

A further group of adult male Winstar rats are confined to a diet formulation the same as that shown in Example 1, except that barley gum is substituted for the oat gum. During the first four weeks, a decline in the average serum cholesterol level of the group as a whole similar to that experienced in Example 1 is witnessed.

Obviously, modifications of this invention are possible. It is understood, therefore, that this application is intended to cover any variations, uses, or adaptations of the invention as may be considered to be known or customary practice in the the art to which this invention pertains.

Having fully described and disclosed the invention, what is claimed and desired to be secured by Letters Patent of the United States is:

1. The method of lowering blood cholesterol which comprises orally administering to an animal an effective amount of oat gum.

2. The method of claim 1 wherein the amount of oat gum administered is from 0.01 percent to 0.1 percent of body weight per day.

3. The method of claim 1 wherein the amount of oat gum administered is from 0.1 percent of 0.5 percent of body weight per day.

4. The method of claim 1 wherein the amount of oat gum administered is from 0.5 percent to 1.0 percent of body weight per day.

5. The method of lowering blood cholesterol which comprises orally administering to an animal an effective amount of a barley gum.

6. The method of claim 5, wherein the amount of barley gum administered is from 0.1 percent to 0.1 percent of body weight per day.

7. The method of claim 5, wherein the amount of barley gum administered is from 0.1 percent to 0.5 percent of body weight per day.

8. The method of claim 5, wherein the amount of barley gum administered is from 0.5 percent to 1.0 percent of body weight per day.

* * * * *

UNITED STATES PATENT OFFICE
CERTIFICATE OF CORRECTION

PATENT NO. : 4,175,124
DATED : November 20, 1979
INVENTOR(S) : Roy G. Hyldon; John S. O'Mahony It is certified that error appears in the above-identified patent and that said Letters Patent are hereby corrected as shown below:

In Claim 3, Line 2, "0.1 percent of 0.5 percent"

should read --0.1 percent to 0.5 percent--.

In Claim 6, Lines 2 and 3, "0.1 percent to 0.1 percent"

should read --0.01 percent to 0.1 percent--.

Signed and Sealed this

Twelfth Day of February 1980

[SEAL]

Attest:

SIDNEY A. DIAMOND

Attesting Officer

Commissioner of Patents and Trademarks